(12) United States Patent
Kitamura et al.

(10) Patent No.: US 6,724,477 B2
(45) Date of Patent: Apr. 20, 2004

(54) INSPECTION METHOD FOR LENS PRODUCTS, AND APPARATUS FOR THE SAME

(75) Inventors: Masatoshi Kitamura, Tokyo-to (JP); Hisamitsu Kawaguchi, Tokyo-to (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 91 days.

(21) Appl. No.: 10/000,541

(22) Filed: Oct. 24, 2001

(65) Prior Publication Data
US 2002/0063862 A1 May 30, 2002

(30) Foreign Application Priority Data
Nov. 28, 2000 (JP) ........................ 2000-360677

(51) Int. Cl.[7] .................. G01N 21/00; G01N 21/01
(52) U.S. Cl. .................. 356/239.2; 356/244; 356/237.1
(58) Field of Search ............... 356/244, 239.2, 356/237.1, 239.1, 239.7, 239.8; 264/1.32, 1.34, 1.7, 2.6, 2.7

(56) References Cited

U.S. PATENT DOCUMENTS

| | | | | |
|---|---|---|---|---|
| 3,519,362 A | * | 7/1970 | Cardno et al. | 356/239.1 |
| 3,711,205 A | * | 1/1973 | Tulk et al. | 356/389 |
| 5,491,332 A | * | 2/1996 | Inbar et al. | 250/221 |
| 6,088,941 A | * | 7/2000 | Inbar et al. | 40/361 |
| 6,275,286 B1 | * | 8/2001 | Haubold et al. | 356/239.1 |
| 2001/0002862 A1 | * | 6/2001 | Okahira et al. | 356/237.1 |

* cited by examiner

Primary Examiner—Russell Adams
Assistant Examiner—Andrew Sever
(74) Attorney, Agent, or Firm—Ladas & Parry

(57) ABSTRACT

An inspection method that enables efficient inspection operations before the shipment of a sheet lens product. A sheet-like Fresnel lens sheet having a masking material bonded on its light-incidence surface is placed on an operation surface equipped with a black color system of background with the light-incidence surface up. On the operation surface the masking material is exfoliated. At the same time the Fresnel lens sheet is inspected by the reflected light to thereby make an inspection of the presence or absence of a white color system of defects. Thereafter, the Fresnel lens sheet is inspected by a the transmission light.

13 Claims, 8 Drawing Sheets

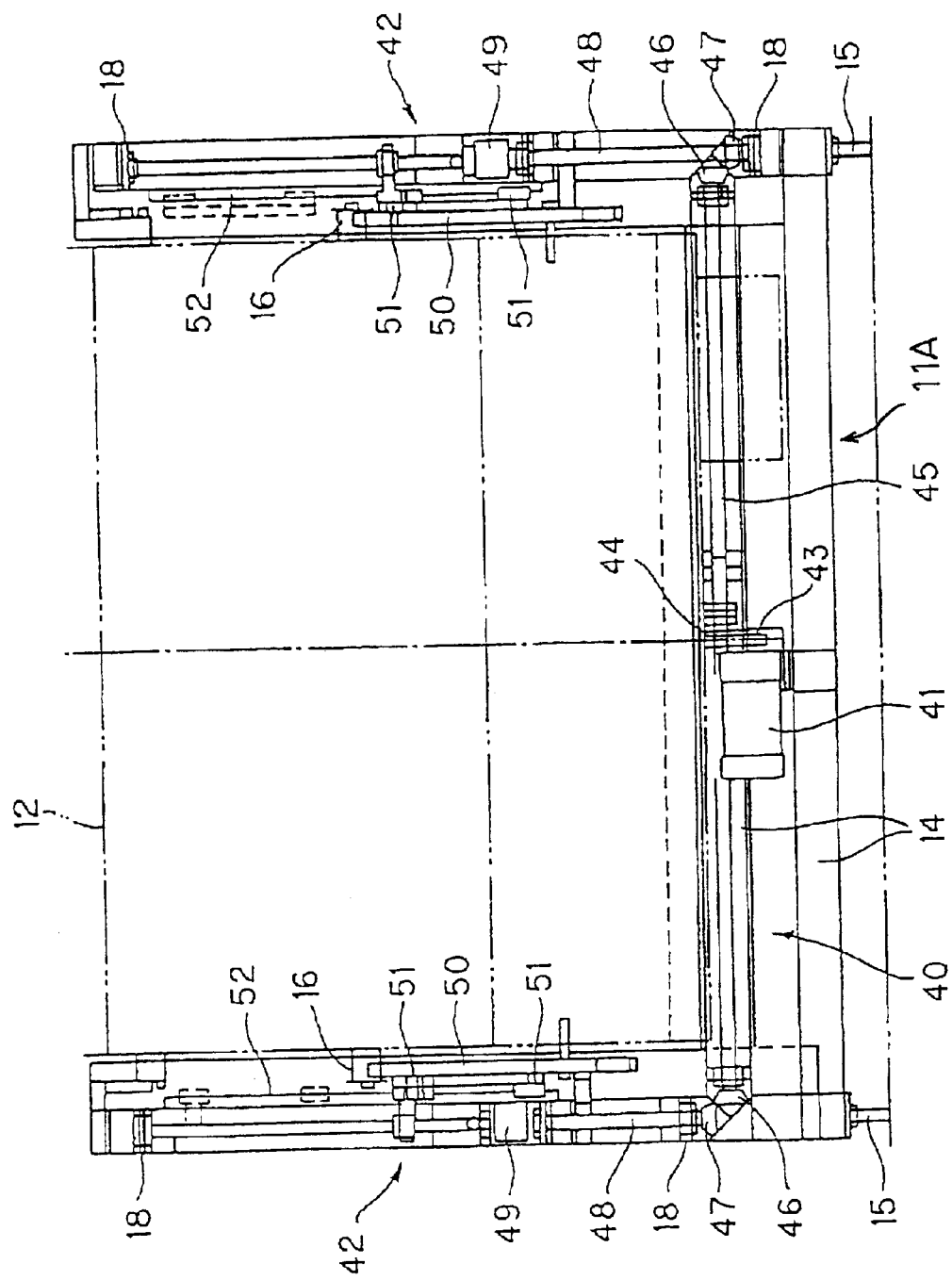

INSPECTION METHOD FOR LENS PRODUCTS, AND APPARATUS FOR THE SAME

BACKGROUND OF THE INVENTION

1. Field of the Invention

The present invention relates to an inspection method for lens products such as a Fresnel lens sheet.

2. Description of the Related Art

In the manufacturing process of a Fresnel lens sheet, a masking material is bonded to the reverse surface of the Fresnel lens sheet (the reverse surface to the surface having formed thereon the Fresnel lens elements), to protect the product during the manufacturing process. And before shipping the product, there is the need to strip off the masking material. In some cases, an antistatic agent or a low-reflection agent is sealed beforehand between the masking material and the reverse surface of the Fresnel lens sheet. In this case, after stripping off the masking material, there is also the need to evenly coat and spread the antistatic agent or the like onto, or over, the entire reverse surface of the Fresnel lens sheet. Further, before shipment, it is necessary to inspect whether or not defects in the lens product exist. As for these defects, there are two kinds of defects. One is a white color defect including a whitish-muddy color of the resin constituting the lens product. The other is a black color defect that results from the entry of foreign substances. Regarding these defects, the presence or absence thereof is determined by separate inspections.

In a conventional inspection method, the following three operations are respectively separately performed. The first operation is the operation for stripping off the masking material. The second operation is the operation for coating the antistatic agent, or the like. And the third operation is the operation for inspecting the above-described two kinds of defects. For this reason, the number of the operation steps that are needed before shipment increases. This lowers the productivity of the lens product and increases the cost thereof.

SUMMARY OF THE INVENTION

An object of the present invention is to provide an inspection method that enables the inspection operation, which is needed before shipment, to be performed with a high efficiency, and an inspection apparatus that is used for the execution of the inspection method.

To achieve the above object, there is provided an inspection method for lens products comprising the steps of: placing a sheet-like lens product, a one-side surface thereof having a masking material overlaid thereon, on an operation surface having a black color system of background, with the a masking surface thereof facing up; stripping off the masking material while the lens product is placed on the operation surface and inspecting the lens product through the use of a reflected light; and thereafter inspecting the lens product through the use of a transmission light.

According to the above-described inspection method, the lens product is inspected on the operation surface with a black color system background. The white color defects of the lens product can be easily found with the use of the reflected light from the lens product. In addition, the apparatus is arranged such that the masking material is stripped off on the operation surface. Therefore, after stripping off the masking material, there is no need to newly re-dispose the lens product onto another inspection base in order to inspect of white color defects. Therefore, the operation of stripping off the masking material and the operation of inspecting for white color defects can be simultaneously or continuously performed with high efficiency.

In the above-described inspection method, it is preferable to strip off the masking material while the lens product placed on the operation surface is grounded. By employing such a method, even when the lens product is made of resin, the static electricity that is produced when stripping off the masking material is grounded. Accordingly, no high-voltage static electricity accumulates in the lens product.

The apparatus may be arranged so that, after stripping off the masking material, the inspection based on the use of the reflected light is preformed while a prescribed kind of treating agent is coated onto, and spread over, the entire surface of the lens product. By employing such an inspection, it is possible to inspect the presence or absence of defects while the treating agent is evenly coated onto, and spread over, the entire surface of the lens product, by simultaneously observing the lens product over its entire surface. Accordingly, the operation efficiency is enhanced and it is possible, at the same time, to reliably prevent the missing of an inspection. The treating agent may be of any kind only if it is to be coated on the surface of the lens product. As an example, in case of a resin-made lens product, an antistatic agent may be coated onto the lens product. Such a treating agent may be disposed between the masking material and the lens product, or, may be newly coated onto the lens product after stripping off the masking material.

In the inspection method of the present invention, the lens product may be detached from the operation surface so that the inspection made with transmission light be performed where the lens product is positioned to shade the illumination light with respect to the inspection position. With this inspection, after completing the inspection for white colors defects, it is possible to see the lens product through the illumination light and determine the presence or absence of black colors defects during a series of operations of detaching the lens product from the operation surface and transferring it to another place. Accordingly, it is not necessary to add another independent inspection process to perform only the inspection for black color defects. Resultantly, the efficiency of the inspection operation increases.

On the other hand, in the inspection method of the present invention, the following measures may also be taken. Namely, an inspection base may be prepared that makes selectable a black color system of background and a white color system of background and that can apply the transmission illumination to the white color system of background from inside the inspection base, whereby the background is switched to the black color system to thereby perform a series of operations before the inspection based on the use of the reflected light; and, thereafter, the background is switched to the white color system and the transmission illumination is made from inside the inspection base, whereby the inspection based on the use of the transmission light is performed. In this case, every step from the stripping of the masking material up to the inspection based on the transmission light can be performed using only one inspection base. Accordingly, it is possible to save the space In the inspection method of the present invention, the inspection based on the use of transmission light preferably is performed from the light-emission surface side of the lens product. By employing such an inspection, it is possible to inspect the lens product from the side where actual observation is made, so that the reliability of the inspection can be enhanced.

An inspection apparatus of the present invention that is usable for the above-described inspection method one that comprises a box-shaped inspection base, on the surface of which there is provided a transparent panel, whereby, at the position inside the inspection base that can be observed through the panel, there is provided a background portion of the black color system.

According to this inspection apparatus looking at the inspection base from its front surface, the background of the panel is colored black. Therefore, with the surface of the inspection base being used as the operation surface, both of the above-described operation of stripping off the masking material and the above-described inspection based on the use of the reflected light can efficiently be performed simultaneously or continuously. Since the panel is transparent, a white-colored transparent background plate is disposed behind the panel, and superposed upon each other. A white color system of transmission illumination is performed from inside the apparatus. By doing so, the inspection based on the transmission light can also be performed on the same operation base.

The background plate may be made to be inserted into and drawn off from behind the panel. By employing such an inspection, with the lens product being kept placed on the surface of the panel, the background plate can be removably attached, with the results of a high level of convenience.

The inspection base may be capable of changing its position in the vertical direction. In this case, the inspection base is vertically moved according to the change in the inspection position. Thereby, the operator can always observe the respective portions of the lens product from the front surface thereof. As a result of this, enhancement in the operation efficiency and the inspection precision can be expected.

The above-described inspection apparatus may comprise a support base which rotatably supports both side portions of the inspection base, the support base including a motor serving as a drive source, a transmission element for distributing the rotating movement of the motor to each side of the inspection base, a feed screw device for converting the rotating movement transmitted by the transmission element into a straight-line movement, and a support member for transmitting the straight-line movement converted by the feed screw device to the inspection base to thereby vertically move the inspection base. If the apparatus is thus constructed, the inspection base can be equally elevated at the left and right sides by utilizing the motor serving as a common drive source, with the result being that the reliability or the stability of the operation is enhanced. The speed at which the operation base is raised or lowered may be made adjustable.

At a lower portion of the panel of the inspection base there may be provided a receiving portion for receiving thereon an object to be inspected; and this receiving portion may be capable of its position being changed in the vertical direction. In this case as well, the vertical position of the lens product can be set to a state where the operation is suitably performed.

Another inspection apparatus of the present invention comprises an operation surface that is equipped with a black color system of background and a receiving portion for receiving thereon a sheet lens product at a lower portion of the operation surface, and a grounded electrically conductive portion is provided on the surface of the receiving portion.

According to this inspection apparatus, the lens product is grounded via the electrically conductive portion. Therefore, even when the operation of exfoliating the masking material bonded to the surface of the resin-made lens product, is performed, which is inevitably followed by the production of static electricity, there is no danger of a high-voltage static electricity accumulating in the lens product.

BRIEF DESCRIPTION OF THE DRAWINGS

FIG. 7 is a front view of the inspection apparatus, of which the inspection base is capable of moving up and down.

DESCRIPTION OF THE PREFERRED EMBODIMENTS

Figure 1:
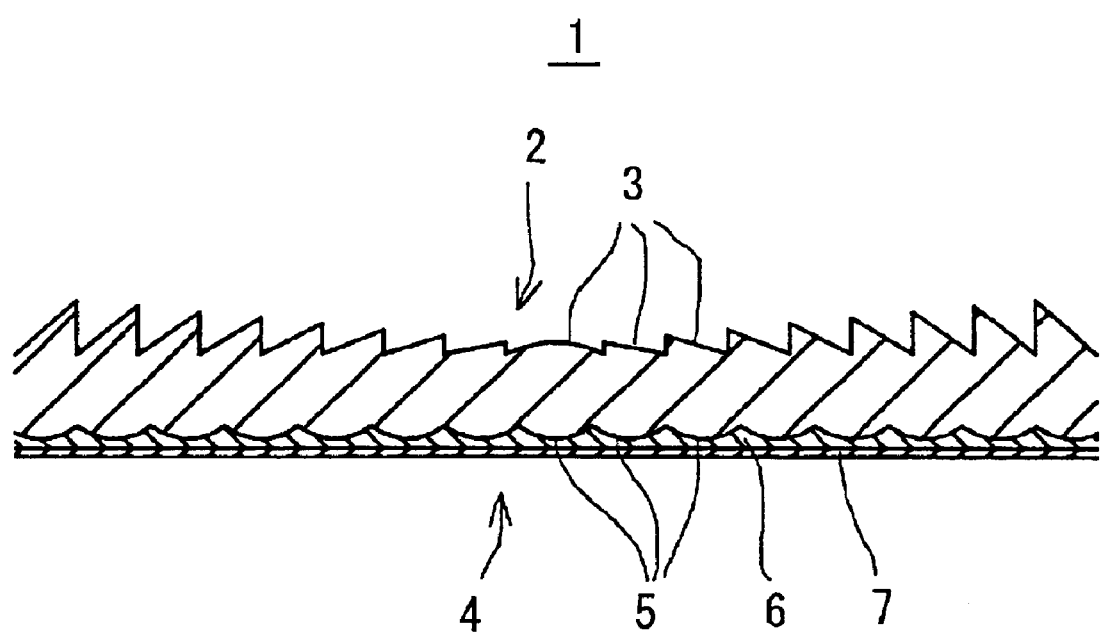
FIG. 1 is an enlarged view of a central part of a Fresnel lens sheet to be pre-determined as an inspection object in an inspection method according to an embodiment of the present invention.

FIG. 1 is an enlarged view of a central part of a Fresnel lens sheet to be pre-determined as an inspection object in an inspection method according to an embodiment of the present invention. The Fresnel lens sheet 1 has a resin-made sheet material, of which the light-emission surface 2 has coaxially formed thereon a number of Fresnel lens elements 3. The material has a light-incidence incident surface 4 on a side opposite to the light-emission surface 2. The light-incidence incident surface 4 has formed thereon a number of lenticular lens elements 5 in the way they are arranged in one direction. The light-incidence surface 4 sometimes is referred to as "the reverse surface of the Fresnel lens sheet". Halfway through the manufacture of the Fresnel lens sheet 1, the light-incidence surface 4 is coated with a treating agent, an antistatic agent 6, or a low-reflection agent or the like. A masking material 7 is then overlaid over the entire surface of the light-incidence surface 4. As a result of this, the light-incidence surface 4 becomes a masking surface. The treating agent is not always coated.

Figure 2:
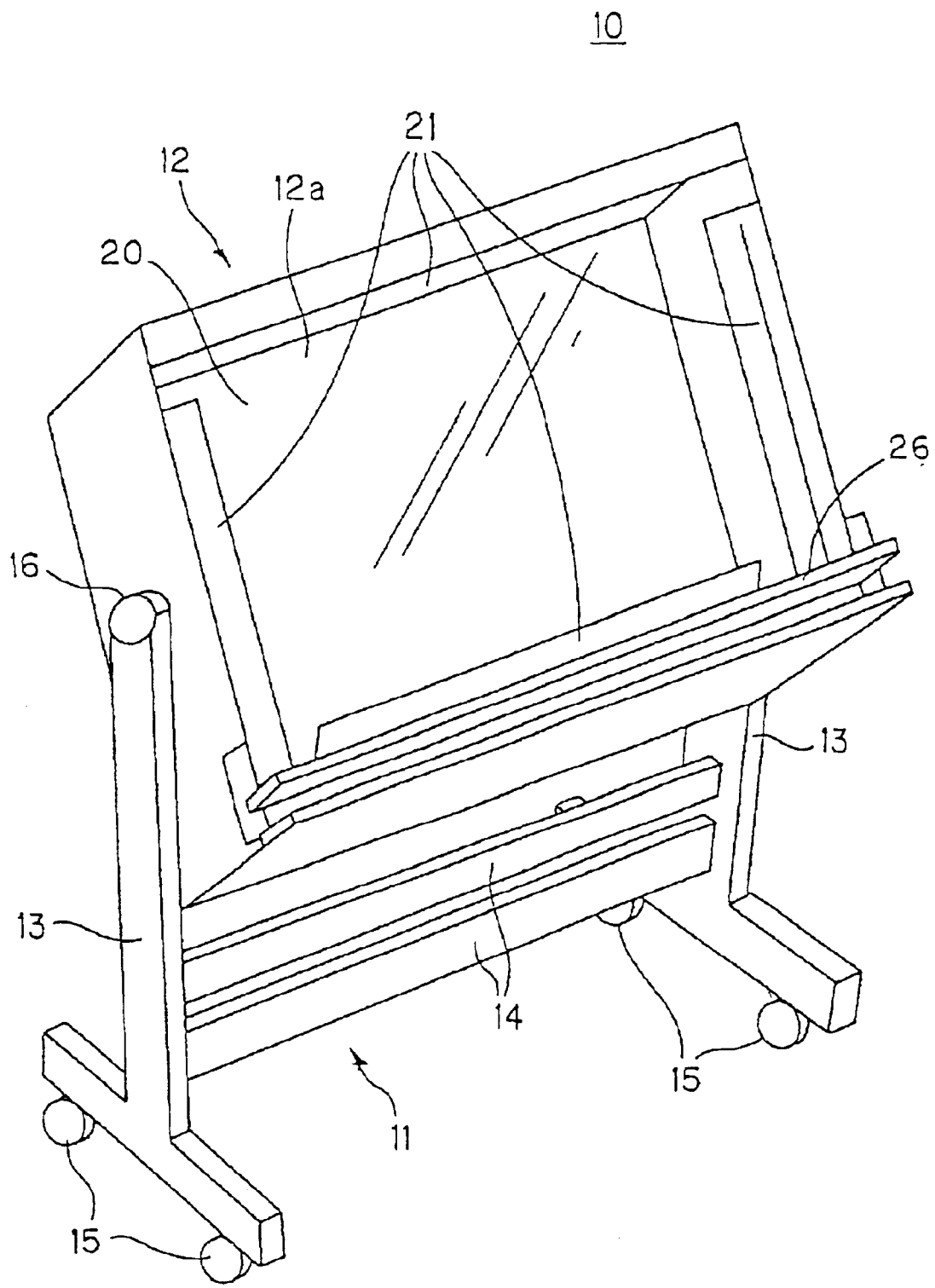
FIG. 2 is a perspective view of the inspection apparatus according to the embodiment of the present invention.

FIG. 2 illustrates an apparatus for inspecting the Fresnel lens sheet 1. The inspection apparatus 10 includes a frame 11 serving as a support base and an inspection base 12 that is supported by that frame 11. The frame 11 includes a pair of support portions 13 and lateral beams 14 that horizontally connect the support portions 13. Each support portion 13 is formed into the shape of an inverted T and, on the underside thereof, there are attached a pair of casters 15 one of which is on the front side and the other of which is on the back side.

The inspection base 12 is attached to the upper end of each support portion 13 via a bearing portion 16. The bearing portion 16 functions to rotatable support the inspection base 12 about a horizontal axis and constrains the inspection base 12 at a given position within a range of rotation so that it may be unrotatable. As a result of this, the inspection base 12 has its inclination adjustable about the horizontal axial line.

Figure 3A:
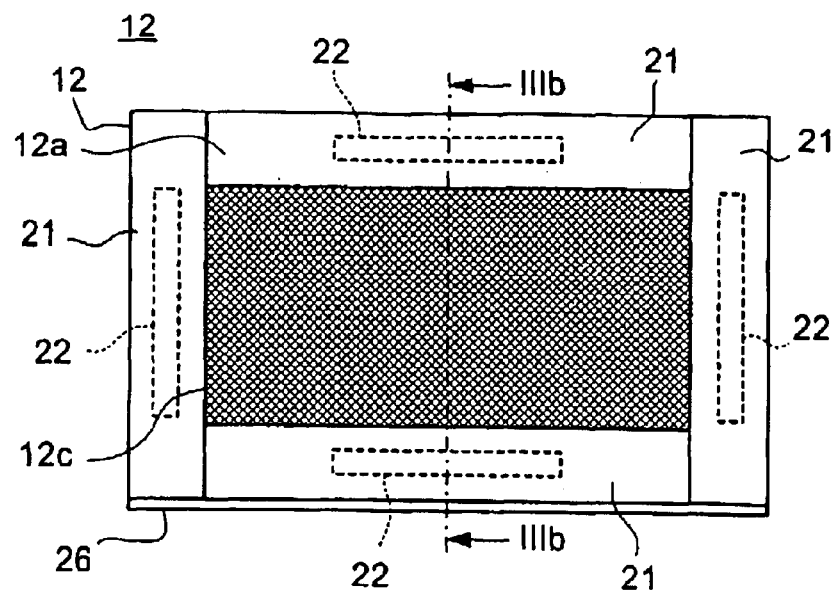
FIGS. 3A, 3B, and 3C are views illustrating the details of an inspection base provided on the inspection apparatus of FIG. 2.
Figures 3B, 3C:
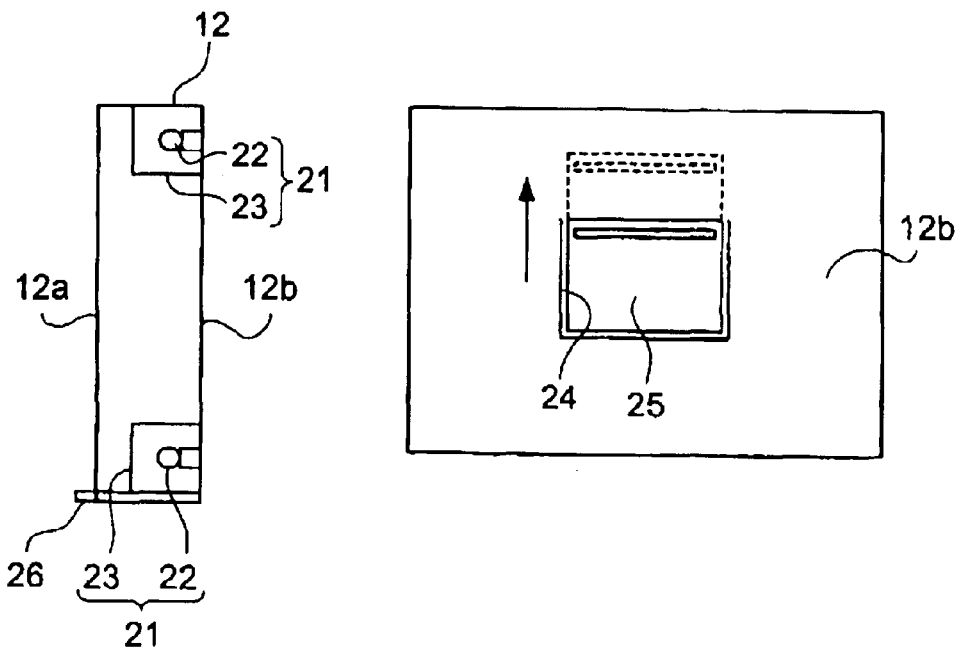

The inspection base 12 is formed into a box shape presenting a rectangular configuration which is elongated in the right and left direction when it is viewed from the side of an operation surface 12a. Into the operation surface 12a there is fitted a transparent panel 20. The panel 20 is constructed of, for example, glass. As illustrated in FIG. 3 as well, at the portion within the inspection base 12 of which observation can be made through the panel 20, there is provided a black-colored background part 12c. Incidentally, FIG. 3A is a front view of the inspection base 12, FIG. 3B is a sectional view taken along a line IIIb—IIIb of FIG. 3A, and FIG. 3C is a rear view thereof.

At upper, lower, left, and right parts of the background portion 12c of the inspection base 12, there are provided illumination lamps 21.

Each illumination lamp 21 is equipped with a light source 22 and an illumination cover 23 for covering it. The light source 22 preferably is the one that emits a white color system of illumination light and the use of a fluorescent tube is suitable. The illumination cover 23 preferably is the one that similarly can produce a white color system of illumination light and, suitably, an acrylic cover that is colored milky is used. Instead of the acrylic cover, there may be used for the illumination cover 23 various kinds of semi-transparent resins, glass, etc. As illustrated in FIG. 3C, at the rear surface 12b of the inspection base 12, an opening 24 is formed with a purpose of, for example, the replacement of the illumination lamp 21, etc. The opening 24 is closed by a lid 25 that can slide upward through the sliding operation.

Figure 4:
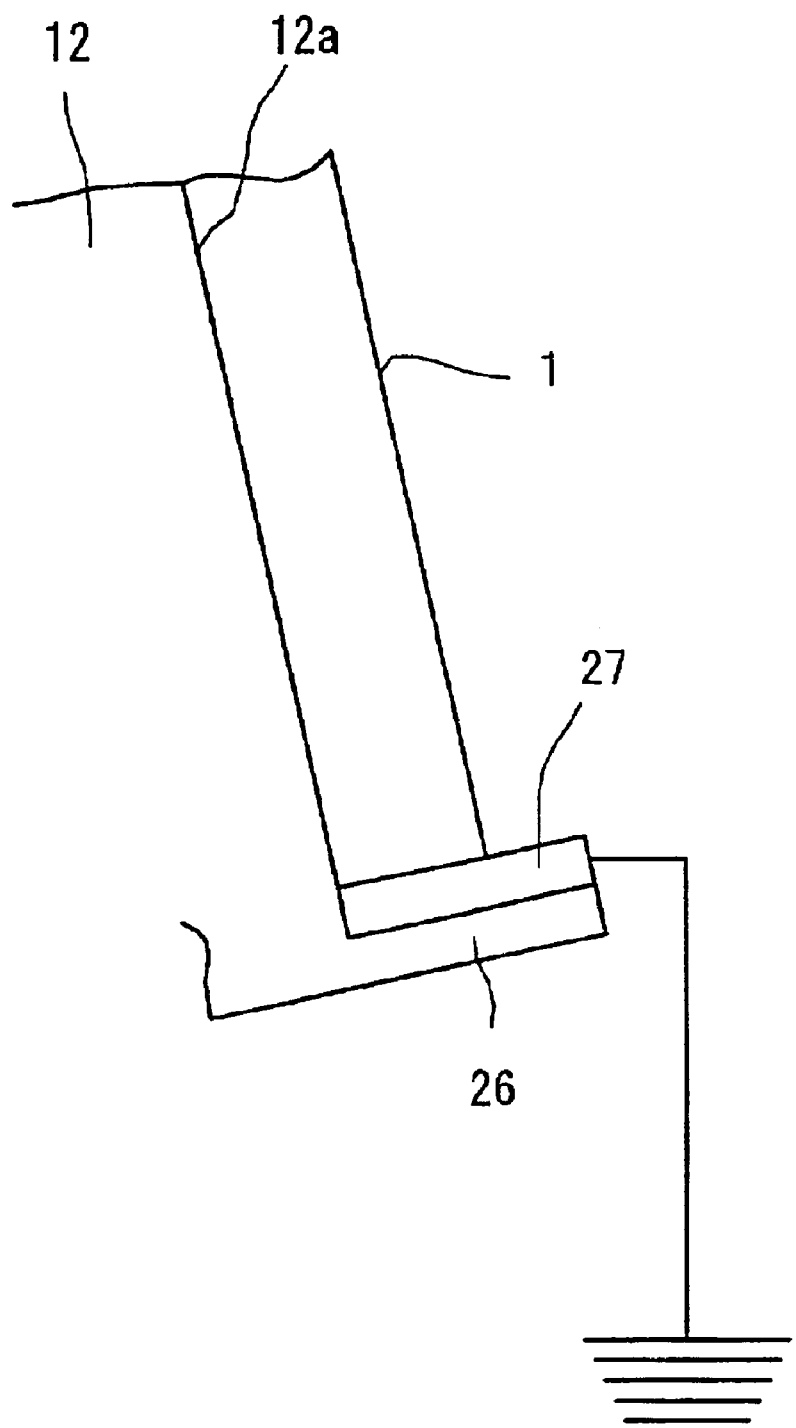
FIG. 4 is an enlarged view of a receiving plate of the inspection base of FIG. 3.

As illustrated in FIG. 4 as well, on a lower end of the operation surface 12a of the inspection base 12 there is provided a receiving plate 26 for placing a lens product such as the Fresnel lens sheet 1. An electrically conductive mat 27 is laid on the upper surface of the receiving plate 26. That mat 27 is grounded at a suitable position. Accordingly, the receiving plate 26 corresponds to a receiving portion, while the mat 27 functions as the electrically conductive portion of that receiving portion.

Figure 5A:
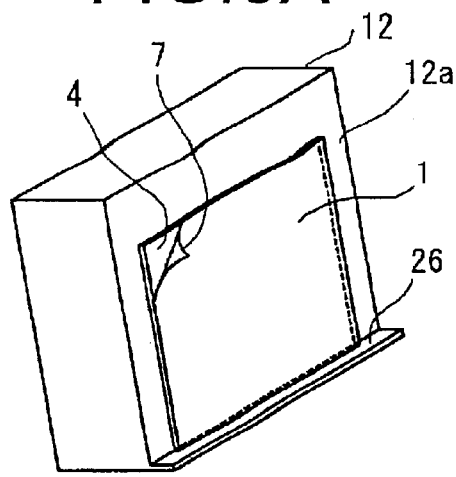
FIGS. 5A, 5B, and 5C are views illustrating parts of the procedure for performing the inspection operation based on the use of the inspection base of FIG. 2.

Next, with reference to FIGS. 5A to 5C, an explanation will be given of the procedure for inspecting the Fresnel lens sheet 1 of FIG. 1 through the use of the inspection apparatus 10. First, as illustrated in FIG. 5A, the Fresnel lens sheet 1 is placed on the operation surface 12a so that the light-incidence surface 4 (the reverse surface of the Fresnel lens sheet) may be directed to the operator side, and the lower end of this lens sheet 1 is supported by the receiving plate 26. And, the masking material 7 is stripped off. At this time, the static electricity that has been produced as a result of the stripping-off of the masking material 7 is grounded via the mat 27. Therefore, there is no excessively large amount of static electricity being accumulated in the Fresnel lens sheet 1.

Figure 5B:
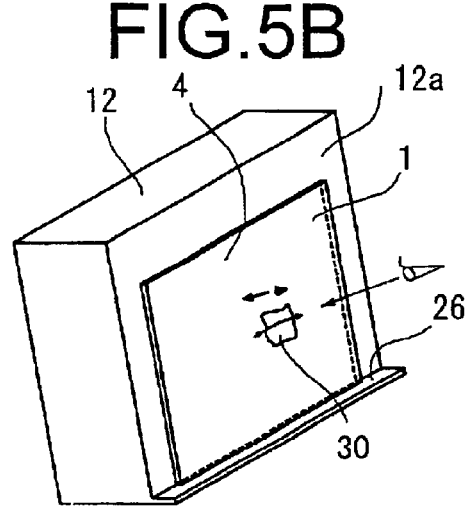
Figure 5C:
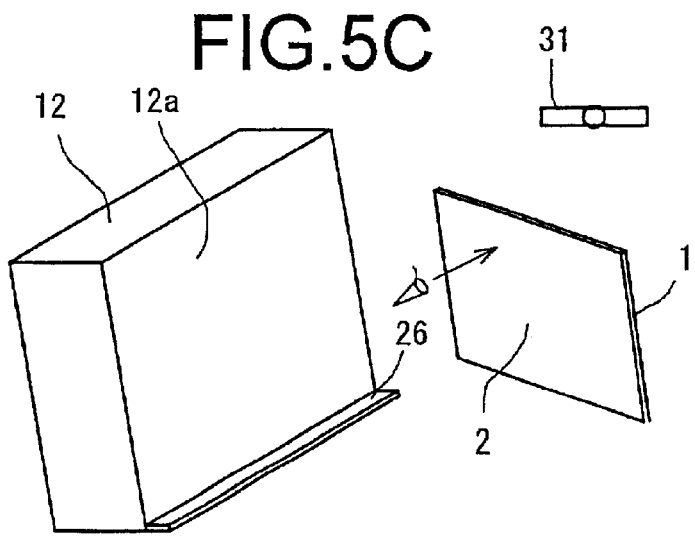

Next, as illustrated in FIG. 5B, the light incidence surface 4 is wiped off by a waste 30. By doing so, the antistatic agent 6 which exists between the masking material 7 and the light-incidence surface 4 is uniformly coated and spread over the entire surface of the light incidence surface 4.

During the time period in which the masking material 7 is stripped off and the antistatic agent 6 is spread, jointly with these operations, the operator visually inspects the presence or absence of the defects of the Fresnel lens sheet 1. At this time, the illumination lamp 21 is lit, whereby the Fresnel lens sheet 1 is inspected on the black-colored background within the inspection base 12. In this state, the inspection is carried out through the use of the reflected light of the external light that has come into the light-incidence surface 4 of the Fresnel lens sheet 1. Accordingly, it is possible to easily find white color defects such as whitish-muddy colors, scratches of lens, etc.

After completion of the inspection, subsequently, while the Fresnel lens sheet 1 is being reversed so that the light-emission surface 2 (see FIG. 1) may be directed toward the operator side, the lens sheet is taken out from the inspection base 12. Thereby, as shown in FIG. 5C, inspection for the presence or absence of the defects is done while the Fresnel lens sheet 1 is disposed as light is shaded from an illumination lamp 31 in the inspection place. This inspection is performed by the use of the transmission light that emits from the illumination lamp 31 and that transmits through the Fresnel lens sheet 1. Accordingly, it is possible to easily find black color defects such as entry of foreign substances. Incidentally, in place of the illumination light 31, the inspection may be performed through the use of the transmission light that is the external light (the sunlight, etc.) incident upon the inspection place.

As described above, according to the inspection procedure of this embodiment, the following two operations are parallel-performed on the operation surface 12A. One is the operation of stripping off the masking material 7 and uniformly coating and spreading the antistatic agent 6. The other is the operation of inspecting for white color defects of the Fresnel lens sheet 1. Thereafter, when detaching the Fresnel lens sheet 1 from the inspection base 12, black color defects are inspected. Therefore, it is possible to enhance the efficiency of the inspection operation by efficiently performing that series of operations.

Figure 6A:
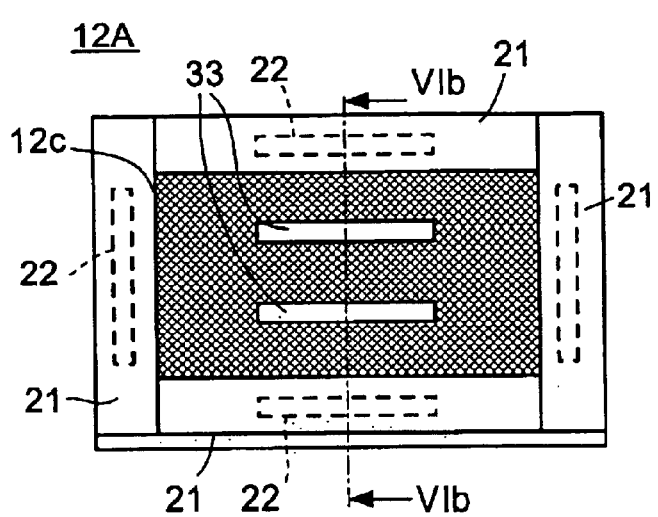
FIGS. 6A, 6B, 6C, and 6D are views of another embodiment of the inspection base.
Figure 6B:
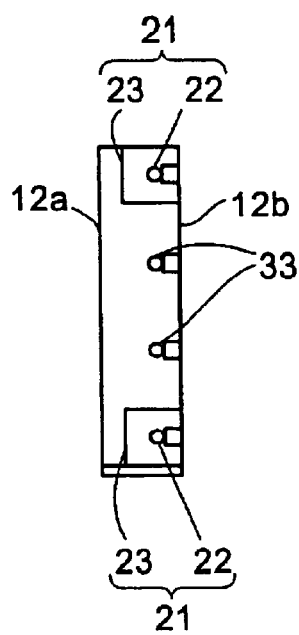
Figure 6C:
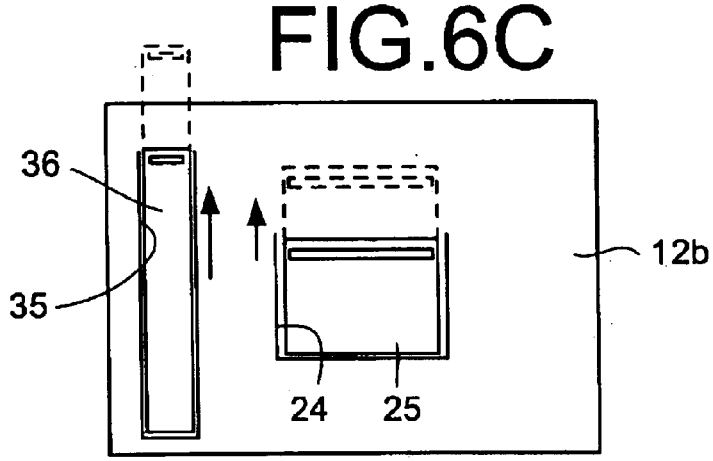
Figure 6D:
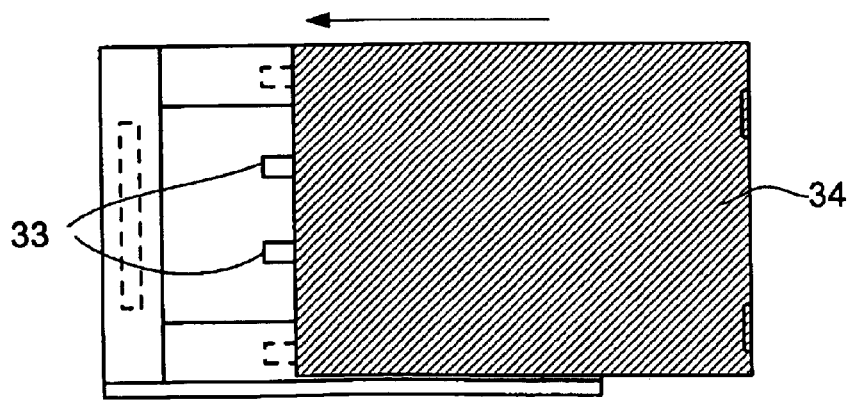

FIGS. 6A, 6B, 6C, and 6D illustrate another inspection base of the present invention. It is to be noted that this inspection base is the one that is prepared by partially changing the inspection base 12 of FIGS. 3A to 3C. Therefore, the common portions to those of FIGS. 3A to 3C are denoted by like reference numerals and the relevant explanation may be omitted. FIG. 6A is a front view of the inspection base; FIG. 6B is a sectional view taken along a line VIb—VIb of FIG. 6A; FIG. 6C is a rear view; and FIG. 6D is a view illustrating the state of the inspection base at the time of performing specified inspection.

The inspection base 12A shown in FIGS. 6A to 6D differs from the inspection base 12 shown in FIGS. 3A to 3C in the following respects. First two illumination lamps 33 are added to the background part 12c. Second, a background plate 34 is made removably attachable on the operation surface 12a. Third, a working opening 35 is added to a rear surface 12 band; this opening 35 is closed by a lid 36 that is slide-operable in the upward direction. Incidentally, the illumination lamp 33 is only constructed of the light source 22 illustrated in FIGS. 3A and 3B, and the illumination cover 23 is omitted. The background plate 34 is constructed of a semi-transparent plate member that is colored into a white color system. For the material of that background plate 34, for example, an acrylic plate is used. The background plate 34 is made to be inserted into and drawn off from the rear-surface side of the panel 20 that is provided on the operation surface 12a of the inspection base 12A. The working opening 35 is provided for the purpose of preventing the background plate 34 from being flexed to thereby contact the illumination lamp 33 when performing insertion and draw-off of that background plate 34. It therefore is provided so that, to this end, the operator may put his or her hand into the opening 35 from the reverse side to thereby support the background plate 34.

According to the above-described inspection base 12A, it is possible to insert the background plate 34 behind the panel 20 and light up the illumination lamps 21 and 33. It is thereby possible to emit a white color system of transmission light from behind the panel 20. Accordingly, the inspections for black color system of defects with the use of the transmission light can be performed on the operation surface 12a. It is to be noted that the inspection of a black color system of defects, based on the use of the inspection base 12A, can be performed not only to the Fresnel lens sheet 1 but also to other resin-made sheet-like lens products such as a lenticular lens sheet, etc.

Figure 8:
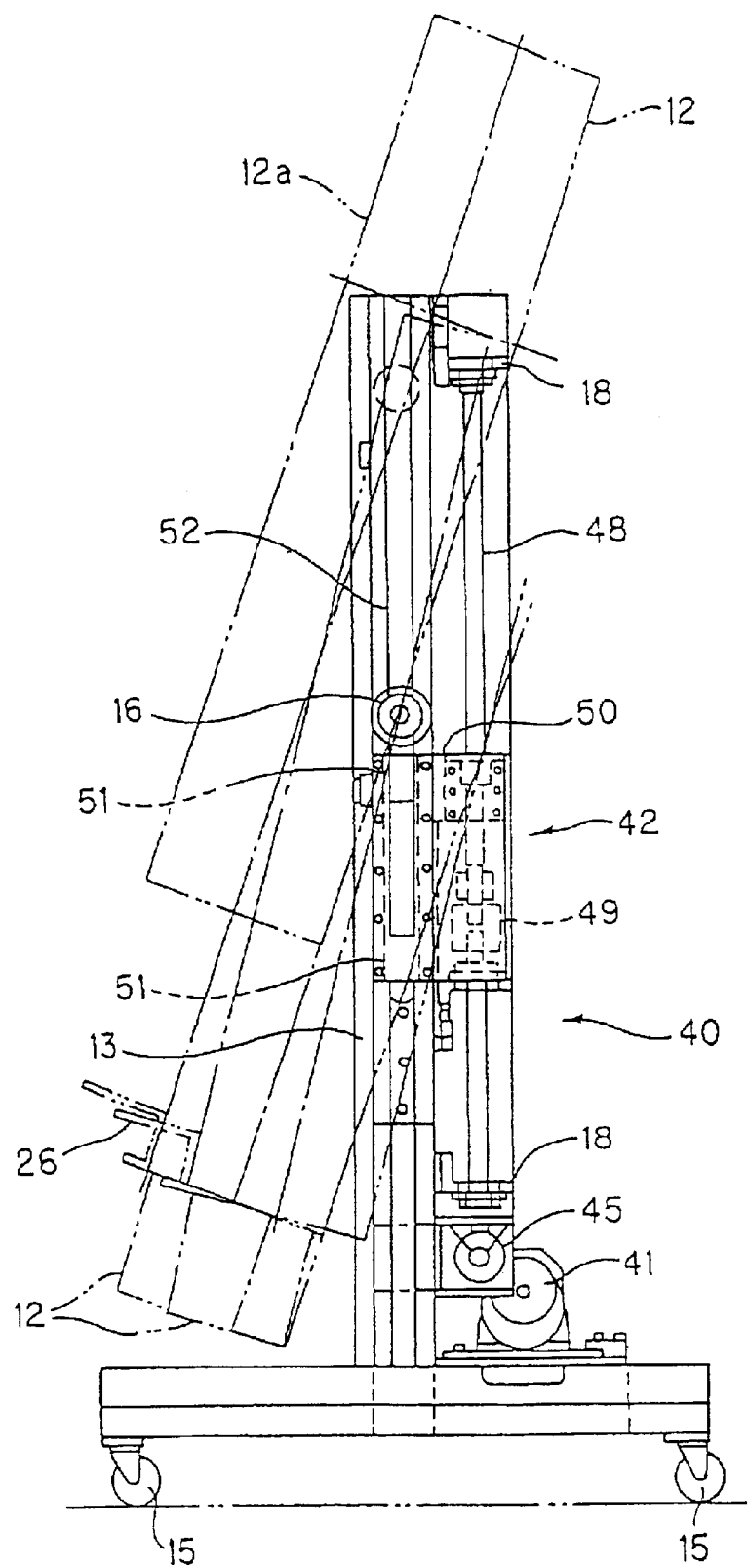
FIG. 8 is a side view, partly broken, of the inspection apparatus of FIG. 7.

FIGS. 7 and 8 are views illustrating another embodiment of the frame 11 of the inspection apparatus 10. FIG. 7 illustrates a view from the rear-surface side of the inspection base 12. FIG. 8 view from the side surface thereof. As illustrated in these figures, an elevation mechanism 40 for vertically moving the inspection base 12 is provided on the frame 11A. The elevation mechanism 40 converts the rotating movement of an electric motor 41, serving as a drive source, provided substantially at the centers of the lateral beam 14, into vertical straight-line movements, through the utilization of ball-screw devices 42 each provided on the support portion of the frame 11. By doing so, the supports 50 of each of that supports the inspection base 12 are vertically raised and lowered.

The rotating movement of the electric motor 41 is transmitted to a horizontal transmission shaft 45 via a pair of gears 43, 44. The rotation of the horizontal transmission shaft 45 is transmitted to screw shafts 48 of the ball-screw devices 42 via two pairs of bevel gears each of which have been provided on one corresponding end of the shaft 45. The screw shaft 48 is supported on the rear surface of the support portion 13 of the frame 11A via a pair of elevation brackets 18 so that it may be rotatable and axially unmovable.

A ball nut 49 fitted onto the screw shaft 48 is connected to the support 50 serving as a support member. Sliders 51 are attached to the corresponding support 50. The sliders 51 are guided along a vertically extending rail 52 that has been attached to the support-columnar portion 13. A bearing portion 16 is provided on the upper end of the support 50. With the above-described construction, when activating the rotation of the electric motor 41, that rotation is converted into a vertical straight-line movement of the support 50 through the operation of the ball-screw device 42. Thereby, the height of the inspection base 12 that is supported by the bearing portions 16 on the upper end of the respective supports 50 is varied.

If using the inspection apparatus 10 having the inspection base 12, the height of that is adjustable in that way, and the height of the lens product can be adjusted so that the operation position and the observation position of the operator relative to the lens product may always be located in front of the operator. Therefore, the enhancements of the operation efficiency and inspection precision can be expected.

The present invention is not limited to the above-described embodiment and can be executed in various kinds of forms. For example, the inspection method of the present invention can be executed utilizing other equipment than the above-described inspection apparatus 10. For example, it may be arranged so that a desk or an operation bed, or the like, is used to support a lens product. Such equipment may be thereby arranged so that the inspection be performed through the stripping-off of the masking material or through the use of the reflected light. In the case of inspecting the Fresnel lens sheet 1, preferably, the material of the operation mat therefor is constructed of the following quality of material. The material should be of a quality capable of preventing the Fresnel lens element 3 from being crushed when spreading the antistatic agent and, at the same time, preventing the lens sheet 1 from getting out of position. Preferably, polyurethane foam can be used as the material of the operation mat. Regarding the illumination lamps 21, 33 mounted within the inspection base 12, 12A, is preferably one is used that can be adjusted in terms of the amount of light emitted. It is possible to provide a mechanism for elevating the receiving plate 26 of the inspection base 12, 12A along the operation surface 12a. Instead of the above-described elevation mechanism 40, or in addition thereto, the height of the lens product may be adjusted. The lens product that is to be inspected is not limited to the Fresnel lens sheet of FIG. 1, and various kinds of sheet-like lens products may be made to be inspection objects. The treating agent that is coated onto the surface of the lens products is not limited to an antistatic agent. Even when no treating agent is coated, it is possible to apply the inspection method of the present invention.

As has been explained above, according to the inspection method of the present invention, the operation of exfoliating the masking material on the operation surface and inspecting for black color and white color defects, based on the use of the reflected light, are simultaneously or continuously performed. Therefore, it is possible to make efficient various kinds of operations, which are necessary before the shipment of the lens products, to thereby achieve enhancement of the productivity of the lens products and the reduction in the cost thereof. Also, according to the inspection apparatus of the present invention, it is possible to easily realized an environment that suits the execution of the inspection method of the present invention.

What is claimed is:

1. An inspection method for a sheet-like lens product having a masking material overlaid on a surface of said lens product, comprising the steps of:

placing the lens product, on an operation surface having a black color background, with the surface of the lens product having the masking material facing up;

stripping off the masking material and inspecting the lens product through the use of a reflected light, while the lens product is being placed on the operation surface; and thereafter inspecting the lens product through the use of a transmission light.

2. The inspection method according to claim 1, wherein the operation surface is grounded.

3. The inspection method according to claim 1, wherein after stripping off the masking material, the inspection by the use of the reflected light is performed while a prescribed kind of treating agent is coated and spread over the whole surface of the lens product.

4. The inspection method according to claim 1, wherein the lens product is detached from the operation surface, and inspection by the use of the transmission light is performed in such a manner that the lens product is positioned to shade an illumination light that is applied to the inspection position.

5. The inspection method according to claim 1, wherein an inspection base is prepared that allows selection of a black color background and a white color background, and that can apply the transmission light to the white color background from inside the inspection base, and whereby the background is switched to the black color background to perform a series of operations by use of the reflected light; and, thereafter, the background is switched to the white color background and the transmission light is applied from inside the inspection base, whereby the inspection by the use of the transmission light is performed.

6. The inspection method according to claim 1, wherein the inspection by the use of the transmission light is performed from a light-emission surface side of the lens product.

7. An inspection apparatus comprising:
   a box-shaped inspection base;
   a transparent panel provided on a surface of the inspection base; and,
   a black color background portion observable through the transparent panel.

8. The inspection apparatus according to claim 7, further comprising a white-colored translucent background plate that is detachably disposed to be superposed upon the transparent panel, and wherein an illumination lamp capable of emitting a white color illumination light is provided inside the inspection base.

9. The inspection apparatus according to claim 8, wherein the background plate can be inserted into and drawn off from behind the panel.

10. The inspection apparatus according to claim 8, wherein the inspection base is selectively positionable in the vertical direction.

11. The inspection apparatus according to claim 8, further comprising a support base that rotatably supports both side portions of the inspection base, wherein the support base includes a motor serving as a drive source, a transmission element for distributing the rotating movement of the motor to each side of the inspection base, a feed screw device for converting the rotating movement transmitted by the transmission element into a straight-line movement, and a support member for transmitting the straight-line movement converted by the feed screw device to the inspection base to thereby vertically move the inspection base.

12. The inspection apparatus according to claim 7, wherein at a lower portion of the panel of the inspection base there is provided a receiving portion for receiving an object for inspection; and the receiving portion is selectively positionable in the vertical direction.

13. An inspection apparatus comprising: an operation surface equipped with a black color background; and
   a receiving portion provided at a lower portion of the operation surface for receiving thereon a sheet lens product, wherein a surface of the receiving portion is provided with a grounded conductive portion.

* * * * *